(12) United States Patent
Bunschoten et al.

(10) Patent No.: US 7,943,602 B2
(45) Date of Patent: May 17, 2011

(54) PHARMACEUTICAL APPLICATION OF 15- OR 16-SUBSTITUTED TESTOSTERONE ANALOGUES

(75) Inventors: Evert Johannes Bunschoten, Heesch (NL); Herman Jan Tijmen Coelingh Bennink, Driebergen (NL); René Frank Van Der Linden, Maarn (NL)

(73) Assignee: Pantarhei Bioscience B.V. (NL)

( * ) Notice: Subject to any disclaimer, the term of this patent is extended or adjusted under 35 U.S.C. 154(b) by 214 days.

(21) Appl. No.: 10/526,730

(22) PCT Filed: Sep. 5, 2003

(86) PCT No.: PCT/NL03/00621
§ 371 (c)(1),
(2), (4) Date: Sep. 16, 2005

(87) PCT Pub. No.: WO2004/022065
PCT Pub. Date: Mar. 18, 2004

(65) Prior Publication Data
US 2006/0122158 A1      Jun. 8, 2006

(30) Foreign Application Priority Data

Sep. 5, 2002  (EP) ..................................... 02078643

(51) Int. Cl.
*A61K 31/57* (2006.01)
*A61K 31/56* (2006.01)
(52) U.S. Cl. .......................... 514/171; 514/170; 514/178
(58) Field of Classification Search .................. 514/170, 514/171, 17, 8
See application file for complete search history.

(56) References Cited

U.S. PATENT DOCUMENTS 2,793,216 A * 5/1957 Murray et al. ................. 552/612
6,117,446 A * 9/2000 Place ............................ 424/435

FOREIGN PATENT DOCUMENTS

| FR | 2.035.786 A | 12/1970 |
| GB | 774064 A | 5/1957 |
| WO | WO 00/74684 A1 | 12/2000 |
| WO | WO 01/23405 A2 | 4/2001 |

OTHER PUBLICATIONS

Wood, et al., "Regio- and Stereoselective Metabolism of Two C19 Steroids by Five Highly Purified and Reconstituted Rat Hepatic Cytochrome P-450 Isozymes", Journal of Biological Chemistry, 1983, 258 (14), pp. 8839-8847.*
Yamazaki, "Progesterone and Testosterone Hydroxylation by Cytochromes P450 2C19, 2C9, and 3A4in Human Liver Microsomes1", Archives of Biochemistry and Biophysics,vol. 346, No. 1, 1997, pp. 161-169.*
Allen et al., "The Reaction of Alkoxalylated Steroid Ketones with Dibenzoyl Peroxide. A Synthesis of 16β-Hydroxytestosterone", J. Org. Chem. (1962), 27(12) 4681-4682.
Yamashita, et al. "Microbial 16β-Hydroxylation of Steroids with *Aspergillus niger*", Agr. Biol. Chem. (1976) 40 (3), 505-509.
Rosenbrock, et al., "Testosterone Metabolism in Rat Brain Is Differentially Enhanced by Phenytoin-Inducible Cytochrome P450 Isoforms", J. of Neuroendocrinology, (1999) 11, 597-604.

* cited by examiner

*Primary Examiner* — Sreeni Padmanabhan
*Assistant Examiner* — Sahar Javanmard
(74) *Attorney, Agent, or Firm* — The Webb Law Firm

(57) ABSTRACT

The invention relates to pharmaceutical dosage units for oral, transmucosal or transdermal administration containing 15- or 16-substituted testosterone analogues, as well as to therapeutic methods that employ these testosterone analogues. More particularly, the invention is concerned with such pharmaceutical dosage units containing at least 10 μg of an androgenic steroid selected from the group consisting of 15-hydroxytestosterones, 16-hydroxytestosterones, precursors thereof and mixtures of these hydroxytestosterones and/or their precursors; and a pharmaceutically acceptable excipient. The term "15-hydroxytestosterones" encompasses both 15α-hydroxytestosterone (15α, 17β-dihydroxy-4-androsten-3-one) and 15β-hydroxytestosterone (15β, 17β-dihydroxy-4-androsten-3-one). Similarly, the term "16-hydroxytestosterones" encompasses both 16α-hydroxytestosterone hydroxytestosterone (16α, 17β-dihydroxy-4-androsten-3-one) and 16β-hydroxytestosterone (16β, 17β-dihydroxy-4-androsten-3-one). The androgenic steroids according to the invention are advantageously employed in e.g. a method of treating or preventing androgen deficiency or a method of hormonal contraception.

10 Claims, 1 Drawing Sheet

PHARMACEUTICAL APPLICATION OF 15- OR 16-SUBSTITUTED TESTOSTERONE ANALOGUES

TECHNICAL FIELD

The present invention is in the field of steroid chemistry. More particularly it relates to pharmaceutical dosage units containing 15- or 16-substituted testosterone analogues, as well as to therapeutic methods that employ these testosterone analogues. The testosterone analogues of the invention possess androgenic activity.

BACKGROUND OF THE INVENTION

British patent GB-B 774,064 is concerned with a process for the production of 15-substituted testosterone, particularly 15-hydroxytestosterone. Therapeutic applications of these substances are nowhere mentioned in the patent.

French patent application FR-A 2 035 786 describes veterinary applications of 16α-α-D-glucosiden of 16α,17-dihydroxysteroids. It is stated that these steroids can be used as estrogens to prevent ovulation in animals such as rodents, dogs, cow and sheep. Claim 3 mentions the glucoside of 16α-hydroxytestosterone. Only parenteral administration is mentioned in the French application.

At present, the main therapeutic application of androgenic steroids is in the treatment of hypogonadal males. Methods of treating androgen deficiency comprising the administration of androgens, such as testosterone, dihydrotestosterone, dehydroepiandrosterone and various esters of testosterone, or derivatives and analogues such as mesterolone are known in the art.

Three types of androgen deficiency in males are usually distinguished, i.e. primary androgen deficiency (testicular insufficiency), secondary androgen deficiency (hypothalamo-hypophyseal insufficiency) and androgen deficiency in ageing males (ADAM), also known as "male menopause" or "andropause".

As regards the long-term administration of androgens to males, a distinction can be made between therapy and supplementation. Therapy typically requires relatively high doses that are usually similar to the rate of production of endogenous androgens. Supplementation on the other hand is suitably done with dosages that are below the rate of production of endogenous androgens (i.e. testosterone, dihydrotestosterone and dehydroepiandrosterone).

Because of concerns about undesirable side effects, androgens are only used sparingly in both therapy and hormone supplementation. Indeed, androgens are normally only used for therapy in human males when primary or secondary androgen deficiency has been diagnosed.

Only a few androgens, e.g. dehydroepiandrosterone (DHEA) and 17α-alkylated derivatives of testosterone, are suitable for oral administration because, unlike testosterone, they are largely resistant to hepatic metabolism. However, disadvantages of oral to administration are associated with the bad absorption of these androgens and the relatively high effect they exert on the liver and particular the liver metabolism (Bhasin et al. (1997) J. Clin. Endocr. Metab. 82:3-8). This is why, in existing protocols, androgens are generally administered in the form of 2-3 weekly depot injections or implants.

It has also been suggested in the prior art to use a combination of a progestogen and an androgen in a method of male contraception. In such a method the progestogen is administered in a sufficiently high amount to halt spermatogenesis—leading to azoospermia—and the androgen is co-administered to prevent androgen deficiency which would otherwise result from the administration of the progestogen. Because of concerns about reliability and possible side-effects of the androgenic component, particularly when administered orally, male contraceptive have not yet made it beyond the experimental stage.

Other therapeutic uses of androgens that have been proposed in the prior art include treatment of the wasting syndrome and retro-viral drug induced lipodystrophia in HIV infected individuals, enhancement of recovery of critically ill catabolic individuals, treatment of benign gynaecological disorders hormonal contraception in females, delayed puberty, female-to-male conversion.

As will be apparent from the above, there is an unmet need for androgens that (i) can be used effectively in the above mentioned therapeutic methods without causing undesirable side-effects, (ii) produce a very consistent, i.e. predictable, impact and/or (iii) may be administered in a convenient manner, especially orally.

SUMMARY OF THE INVENTION

The inventors have unexpectedly discovered that steroids which have not been used in therapeutic applications, i.e. 15-hydroxy or 16-hydroxy substituted testosterone analogues, meet the aforementioned requirements.

Surprisingly, it was found that the hydroxytestosterone analogues according to the present invention combine adequate androgenic potency with acceptable oral bioavailability and minimum impact on liver metabolism. Consequently, the present androgens are particularly suited for any therapeutic applications for which androgens have been employed or recommended. The present hydroxytestosterone analogues may also be delivered effectively, particularly in relatively low dosages such as those typically required by females, by transmucosal or transdermal administration.

Another advantage of the hydroxytesterone analogues according to the invention is their predictable and consistent therapeutic impact, which is believed to be related to the efficiency of uptake, their low hepatic effect and/or their low affinity for sex hormone binding globulin (SHBG). In contrast, the therapeutic effect of known androgens that are sometimes administered orally, notably DHEA or 17α-alkylated derivatives of testosterone, is very dependent on an individual's physiology and even his/her diet. Consequently, these androgens are usually applied in relatively high dosages in order to ensure that the minimum effective dosage is achieved in each individual. Naturally such high dosages have the disadvantage that they lead to relative overdosing in some individuals, which in turn is likely to produce pronounced side effects.

DETAILED DESCRIPTION OF THE INVENTION

Figure 1:
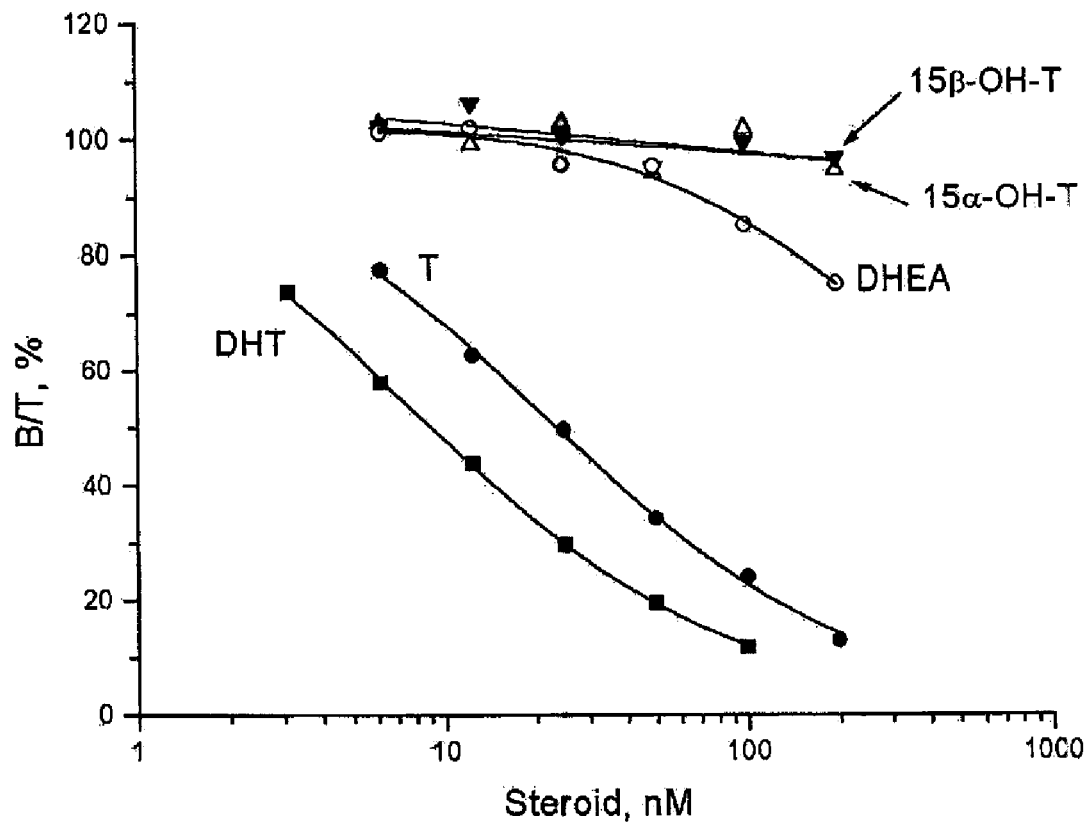
FIG. 1 is a graph of competition curves showing displacement of [$^3$H]DHT from human SHBG using 5α-dihydrotestosterone (DHT), testosterone (T), dehydroepiandrosterone (DHEA), 15α-hydroxytestosterone (15α-OH-T), 15β-hydroxytestosterone (15β-OH-T) as competitors. Results are expressed as bound (B) cpm at each competitor concentration/total (T) cpm bound in absence of competitor as a percentage.

Accordingly, one aspect of the invention relates to a pharmaceutical dosage unit for oral, transmucosal or transdermal administration containing at least 10 μg of an androgenic steroid selected from the group consisting of 15-hydroxytestosterones, 16-hydroxytestosterones, precursors thereof and mixtures of these hydroxytestosterones and/or their precursors; and a pharmaceutically acceptable excipient.

The term "15-hydroxytestosterones" encompasses both 15α-hydroxytestosterone (15α,17β-dihydroxy-4-androsten-3-one) and 15β-hydroxytestosterone (15β,17β-dihydroxy-4-androsten-3-one). Similarly, the term "16-hydroxytestosterones" encompasses both 16α-hydroxytestosterone hydroxytestosterone (16α,17β-dihydroxy-4-androsten-3-one) and 16β-hydroxytestosterone (16β,17β-dihydroxy-4-androsten-3-one).

The term "precursor" as used throughout this document refers to substances which are converted into one of the hydroxytestosterones of the invention following the administration of said precursor to a human subject.

Preferred precursors of the androgenic steroids according to the present invention are derivatives of the present hydroxytestosterones wherein the hydrogen atom of at least one hydroxylgroup has been substituted by an acyl radical of a hydrocarbon carboxylic, sulfonic or sulfamic acid of 1-25 carbon atoms; tetrahydrofuranyl; tetrahydropyranal; or a straight or branched chain glycosydic residue containing 1-20 glycosidic units per residue.

It has been shown that the hydroxytestosterones of the present invention occur in mammals, which means that they offer the important advantage that they can be labelled as natural (Yamazaki et al. Arch Biochem Biophys 1997 Oct. 1; 346(1):161-9). In addition, as can be derived from the aforementioned article, both 15α-hydroxytestosterone, 15β-hydroxytestosterone and 16β-hydroxytestosterone occur in the human body, which means that prima facie the risk of undesired side-effects is lower than is the case for synthetic androgens or natural androgens that are not found in the human body. Thus, in a particularly preferred embodiment of the present invention, the androgenic steroid is selected from the group consisting of 15α-hydroxytestosterone, 15β-hydroxytestosterone, 16β-hydroxytestosterone, precursors thereof and mixtures of these hydroxytestosterones and/or their precursors. Even more preferably, the androgenic steroid is selected from the group consisting of 15α-hydroxytestosterone, 15β-hydroxytestosterone precursors thereof and mixtures of these hydroxytestosterones and/or their precursors.

The present oral dosage units may be prepared according to any method known to the art for the manufacture of pharmaceutical compositions and such units may contain one or more agents selected from the group consisting of sweetening agents, flavouring agents, colouring agents and preserving agents. Said dosage units may suitably contain a non-toxic pharmaceutically acceptable excipient. In case of e.g. tablets, these excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatine or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Examples of dosage unit forms that may be administered by oral route include tablets, soft gelatine capsules, including solutions used in soft gelatine capsules, aqueous or oil suspensions, emulsions, pills, lozenges, troches, syrups, elixirs and the like. Formulations for oral use may also be presented as hard gelatine capsules wherein the active ingredient is mixed with an inert solid diluent, for example calcium carbonate, calcium phosphate or kaolin, or as soft gelatine capsules wherein the steroid component is mixed with water or an oil medium, such as peanut oil, liquid paraffin or olive oil. In a particularly preferred embodiment, the oral dosage units according to the present invention are provided in the form of solid or semi-solid dosage units, especially in the form of tablets, capsules, cachets, pellets, pills, powders or granules.

Aqueous suspensions according to the invention contain the steroids in a mixture with excipients suitable for the manufacture of aqueous suspensions. Such excipients include a suspending agent, such as sodium carboxymethyl-cellulose, methylcellulose, hydroxypropylmethyl-cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the steroid component in a vegetable oil, such as arachide oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the steroid component in a mixture with a dispersing, suspending and/or wetting agent, and one or more preservatives. Suitable dispersing or wetting agents and suspending agents are exemplified by those disclosed above. Additional excipients, for example sweetening, flavouring and colouring agents, may also be present.

The pharmaceutical dosage unit of the invention may also be in the form of oil-in-water emulsions. The oily phase may be a vegetable oil, such as olive oil or arachide oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavouring agents.

Syrups and elixirs may be formulated with sweetening agents, such as glycerol, sorbitol or sucrose. Such formulations may also contain a demulcent, a preservative, a flavouring or a colouring agent.

The steroids of this invention may also be administered in the form of suppositories for rectal or vaginal administration of the drug. These dosage units can be prepared by mixing the steroid with a suitable non-irritating excipient which is solid at ordinary temperatures but liquid at the rectal temperatures and will therefore melt in the rectum to release the drug. Such materials are cocoa butter and polyethylene glycols.

The present dosage unit preferably contains at least 20 μg, more preferably at least 40 μg and most preferably at least 60 μg of the androgenic steroid. In case the dosage unit is meant to provide a sustained release of the androgenic steroid, e.g. in case of a transdermal patch, the amount of androgenic steroid contained in the dosage unit may be as high as 1000 mg. Preferably the amount of the androgenic steroid does not exceed 500 mg, more preferably it does not exceed 200 mg. Most preferably the amount of androgenic steroid in the dosage unit does not exceed 100 mg.

In a particularly preferred embodiment of the invention, the dosage unit is designed for oral administration. Examples of oral dosage units which may suitably be used to deliver the present steroids include tablets, capsules, cachets, pellets, pills, powders or granules.

Typically the present pharmaceutical oral dosage unit has a weight in the range of 0.1-10 grams. The amount of androgenic steroid contained in the oral dosage unit is preferably at least 30 μg, more preferably at least 50 μg and most preferably at least 80 μg. Usually the amount of steroid contained in the oral dosage unit will not exceed 50 mg, more preferably it will not exceed 30 mg, most preferably it will not exceed 20 mg.

The hydroxytesterone analogues of the present invention may advantageously be to employed in a method of male contraception. As mentioned herein before, such a method requires the combined administration of a progestogen and an androgen. Typically the amount of progestogen included in the present dosage unit will exceed 10 μg, preferably it will exceed 30 μg. In a particularly preferred embodiment, the present dosage unit additionally contains a progestogen in an amount equivalent to between 75 and 800 μg, more preferably between 100 and 500 μg levonorgestrel.

In other applications, e.g. in female hormone replacement therapy or female contraception, it may be advantageous to administer the present hydroxytestosterone analogues in combination with an estrogen. Accordingly, the present dosage unit, in addition to the present androgenic steroid, may suitably contain an estrogen, preferably in an amount of at least 10 μg, more preferably in an amount of at least 15 μg.

Examples of progestogens that may employed in the present dosage unit as well as in the methods described herein include progesterone, levonorgestrel, norgestimate, norethisterone, dydrogesterone, drospirenone, 3-beta-hydroxy-desogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, fluorogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nomegestrol, norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nortestosterone, d-17beta-acetoxy-13beta-ethyl-17alpha-ethinyl-gon-4-en-3-one oxime, precursors of these compounds that are capable of liberating these progestogens in vivo when used in the present method and combinations thereof. Preferably the progestogen is selected from the group consisting of progesterone, desogestrel, etonogestrel, gestodene, dienogest, levonorgestrel, norgestimate, norethisterone, drospirenone, trimegestone, dydrogesterone, precursors of these progestogens and combinations thereof.

Examples of estrogens that may suitably be used in accordance with the present invention include ethinyl estradiol, mestranol, quinestranol, estradiol, estrone, estran, estriol, estetrol, conjugated equine estrogens, precursors thereof that are capable of releasing such an estrogen in vivo when used in the present method and combinations thereof. Preferably the estrogen is selected from the group consisting of ethinyl estradiol, estradiol, estetrol and combinations thereof.

Preferred precursors of the androgenic steroids according to the present invention are derivatives of the present hydroxytestosterones wherein the hydrogen atom of at least one hydroxylgroup has been substituted by an acyl radical of a hydrocarbon carboxylic, sulfonic or sulfamic acid of 1-25 carbon atoms; tetrahydrofuranyl; tetrahydropyranal; or a straight or branched chain glycosydic residue containing 1-20 glycosidic units per residue.

Another aspect of the invention relates to a method of curatively or prophylactically treating a mammal, said method comprising oral, transmucosal or transdermal administration to said mammal of the present pharmaceutical dosage unit as described herein before. The term transmucosal administration as used herein, refers to intravaginal, intrauterine, rectal, intranasal, pulmonary, buccal and sublingual delivery, intravaginal delivery being most preferred. The present method is particularly suitable for treating humans.

Oral, rectal, intranasal, buccal and pulmonary administration are ideally suited for (at least) once daily administration. Transdermal administration is advantageously applied at frequencies between once a day and once a month. Intravaginal and intra-uterine administrations are advantageously operated at administration frequencies between once weekly and once monthly.

For reasons of convenience and also to achieve high compliance rates, the present method preferably utilises administration intervals of 1 day, 1 week or 1 month. Regimens that employ once daily oral administration, once weekly transdermal administration or once monthly intravaginal administration are particularly preferred. Most preferably the present method comprises at least once daily administration.

The androgenic steroid(s) of the invention are advantageously administered in an average daily amount which is at least 0.5 μg per kg of bodyweight. Preferably the average daily amount is at least 1 μg per kg of bodyweight, more preferably at least 1.5 μg per kg of bodyweight. The average daily amount usually does not exceed 1.5 mg per kg of bodyweight. Preferably the average daily amount does not exceed 1 mg per kg of bodyweight, more preferably it does not exceed 0.5 mg per kg of bodyweight.

The method according to the present invention is preferably employed in a method of treating or preventing androgen deficiency (in males or females); a method of hormonal contraception (in males or females); a method of treating or preventing wasting syndrome, anti-retroviral drug induced lipodystrophia, lack of well-being or fatigue in HIV infected individuals; a method of reversing catabolic state caused by a chronic illness, surgical intervention, oncological condition, trauma and/or malnutrition; a method of treating or preventing leydig cell dysfunction and germinal epithelial damage following cytotoxic chemotherapy; a method of treating or preventing fatigue or maintaining weight, hemoglobine or neutrophil count during or subsequent to cytotoxic chemotherapy or radiotherapy; a method of treating or preventing benign gynaecological disorders; a method of improving libido (in males or females); a method of treating or preventing delayed puberty; or a method of supporting female-to-male conversion. As mentioned herein before, the administration of the present steroids is particularly advantageous when employed in a method of treating or preventing androgen deficiency, a method of hormonal contraception or a method of treating or preventing benign gynaecological disorders. It is noted that symptoms of androgen deficiency can occur in both males and females. In a particularly preferred embodiment the present is used to treat or prevent androgen deficiency or employed as a contraceptive method in males.

The aforementioned methods usually employ continuous administration of the present steroids during a period of at least 10 days, preferably of at least 20 days. In a particular preferred embodiment the present steroids are administered during a period of at least 100 days with administration-free intervals that do not exceed 10 days, preferably do not exceed 8 days.

In a preferred embodiment, the present method comprises the co-administration of a progestogen in an average daily amount of at least 0.2 μg per kg of bodyweight and/or an estrogen in an average daily amount of at least 0.2 μg per kg of bodyweight. Typically, the average daily amount of co-administered progestogen or estrogen will not exceed 1 mg per kg of bodyweight, more preferably said amount does not exceed 500 μg per kg of bodyweight, most preferably it does not exceed 300 μg per kg of bodyweight.

Yet another aspect of the invention relates to the use of an androgenic steroid selected from the group consisting of 15-hydroxytestosterones, 16-hydroxytestosterones, precursors thereof and mixtures of these hydroxytestosterones and/or their precursors in the preparation of an oral, transmucosal or transdermal dosage unit as described herein. In a particularly preferred embodiment, said androgenic steroid is used in the preparation of a solid or semi-solid oral dosage unit, especially an oral dosage unit in the form of a tablet, a capsule, a cachet, a pellet, a pill, a powder or granules.

The invention is further illustrated by means of the following examples.

EXAMPLES

Example 1

An established competitive steroid binding assay was used to determine the relative binding affinity of 15α-hydroxytestosterone (15α,17β-dihydroxy-4-androsten-3-one), 15β-hydroxytestosterone (15β,17β-dihydroxy-4-androsten-3-one) and 16β-hydroxytestosterone (16β,17β-dihydroxy-4-androsten-3-one) to the androgen receptor (AR). Testosterone (17β-hydroxy-4-androsten-3-one) and 5α-dihydroxytestosterone (DHT, 5α,17β-dihydroxy-androstan-3-one) served as controls in this assay.

The method employed was adapted from the scientific literature and described in detail by Chang et al (1987, J. Steroid Biochem., 27, 1-3, 123-131). Recombinant rat AR was expressed and purified from $E.\ Coli$. The in vitro assays involved the use of AR and [$^3$H]mibolerone, at a fixed concentration of 1.5 nM, as the labeled ligand. Recombinant AR was dissolved in binding buffer (50 mM Tris-Base, pH 7.5, 0.8 mM NaCl, 10% glycerol, 2 mM dithiothreitol, 1 mg/ml BSA and 2% ethanol) and duplicate aliquots were then incubated with [$^3$H]mibolerone at a final concentration of 1.5 nM, together with a vehicle control (1.0% DMSO), or the same amount of vehicle containing increasing concentrations of unlabeled steroid ligands as competitors. After incubation for 4 h at 4° C., the unbound ligands were removed and the amounts of [$^3$H]mibolerone bound to the AR was measured. The average amounts of [$^3$H]mibolerone bound to AR at each concentration of competitor were used to make inhibition curves. IC50 values were subsequently determined by a non-linear, least squares regression analysis. Inhibition constants (Ki) were calculated using the equation of Cheng and Prusoff (Cheng et al., 1973, Biochem. Pharmacol., 22, 3099-3108), using the measured IC50 of the tested compounds, the concentration of radioligand employed in the assay, and the historical values for the Kd of the radioligand, which has been established as 3 nM.

Mean Ki values obtained for 15α-hydroxytestosterone, 15β-hydroxytestosterone, 16β-hydroxytestosterone, testosterone and DHT from three separate experiments are shown in Table 1. For comparision of binding affinities, the Ki value of DHT (which shows the highest affinity) was arbitrarily set at 100% and used to calculate the relative affinities (Table 1). As compared to DHT and testosterone, 15α-hydroxytestosterone, 15β-hydroxytestosterone and 16β-hydroxytestosterone bind with 2 to 3 orders of magnitude less affinity to AR (Table 1).

TABLE 1

Experimentally determined inhibition constants (Ki) for AR binding of 15α-hydroxytestosterone, 15β-hydroxytestosterone, 16β-hydroxytestosterone, testosterone and 5α-dihydroxytestosterone (DHT). Relative binding affinities are also shown, using Ki value of DHT as 100%.

| | AR-binding | |
|---|---|---|
| Trivial Name (Chemical Name) | Ki (nM) | Relative affinity (%) |
| 15α-hydroxytestosterone (4-ANDROSTEN-15α, 17β-DIOL-3-ONE) | 1820 | 0.05 |
| 15β-hydroxytestosterone (4-ANDROSTEN-15β, 17β-DIOL-3-ONE) | 557 | 0.18 |
| 16β-hydroxytestosterone (4-ANDROSTEN-16β, 17β-DIOL-3-ONE) | 814 | 0.12 |
| Testosterone (4-ANDROSTEN-17β-OL-3-ONE) | 2 | 50 |
| 5α-dihydroxytestosterone, DHT (5α-ANDROSTAN-17β-DIOL-3-ONE) | 1 | 100 |

Example 2

To determine the in vivo androgenic potency of 15-substituted testosterone derivatives, 15α-hydroxytestosterone (15α,17β-dihydroxy-4-androsten-3-one) and 15β-hydroxytestosterone (15β,17β-dihydroxy-4-androsten-3-one) were administered orally, once daily, to immature male Wistar rats for 5 consecutive days. Testosterone (17β-hydroxy-4-androsten-3-one) and 5α-dihydroxytestosterone (DHT, 5α,17β-dihydroxy-androstan-3-one), both administered orally, served as positive controls in this bioassay.

15α-hydroxytestosterone, 15β-hydroxytestosterone, testosterone and 5α-dihydroxytestosterone were dissolved in an aqueous suspension of 2% Tween 80, at final test concentrations of 3 mg/ml and 1 mg/ml. Groups of 5 immature male Wistar rats, weighing 50±2 grams, received either vehicle treatment or were administered 30 or 10 mg/kg/day test substance by oral gavage in a dosing volume of 10 ml per kg for 5 consecutive days. During the experiment, animals were housed in cages of 45×23×15 cm and maintained in a controlled temperature of 22-24° C. and humidity (60-80%) environment with 12 hours light/dark cycles. Food (lab diet, rodent diet, PMI nutrition international) and water intake was ad libitum.

The animals were sacrificed 24 hours after receiving the final dose and the wet weight of the seminal vesicle of each animal was recorded and average wet weight per group was calculated. Increase in average seminal vesicle wet weight relative to the average seminal vesicle wet weight of vehicle treated rats was considered indicative for in vivo androgenicity.

In vivo androgenicity data are shown in Table 2. Both 15α and 15β hydroxy-substituted analogues of testosterone induced a dose-dependent and significant increase in seminal vesicle wet weight. These in vivo androgenic effects were similar or equipotent to the dose-dependent effects observed for testosterone and considerably more potent than the in vivo androgenicity observed after oral administration of DHT, a classical androgen and the active metabolite of testosterone in vivo (O'Donnel et al., 1996, Endocrinology, 137, 2703-2710).

TABLE 2

Average increase in seminal vesicle wet weight relative to the average wet weight of vehicle (2% Tween-80) treated animals for groups of 5 immature Wistar rats, treated once daily, orally, for five consecutive days with 15α-hydroxytestosterone, 15β-hydroxytestosterone, testosterone or 5α-dihydroxytestosterone (DHT). Relative androgenic potencies are also shown, using DHT as reference (100%).

| | | In vivo androgenicity | |
|---|---|---|---|
| Trivial Name (Chemical Name) | Oral dose mg/kg/day | Increase seminal vesicle wet weight (%) | Relative potency (%) |
| 15α-hydroxytestosterone (4-ANDROSTEN-15α, 17β-DIOL-3-ONE) | 30 10 | 40 28 | 148 560 |
| 15β-hydroxytestosterone (4-ANDROSTEN-15α, 17β-DIOL-3-ONE) | 30 10 | 35 20 | 130 400 |
| Testosterone (4-ANDROSTEN-17β-OL-3-ONE) | 30 10 | 47 41 | 174 820 |
| 5α-dihydroxytestosterone, DHT (5α-ANDROSTAN-17β-DIOL-3-ONE) | 30 10 | 27 5 | 100 100 |

Example 3

An established competitive steroid-binding assay (Hammond and Lahteenmaki. 1983. Clin Chem Acta 132:101-110) was used to determine the relative binding affinity of 15α-hydroxytestosterone (15α-OH-T), 15β-hydroxytestosterone (15β-OH-T), dehydroepi-androsterone (DHEA), testosterone (T) and 5α-dihydrotestosterone (DHT) for human sex Hormone Binding Globulin (SHBG).

Human SHBG was purified from transgenic mouse serum, as described previously (Avvakumov G V et al., 2000. J Biol Chem 275: 25920-25925). The human SHBG prepared in this way was assessed to be >99% pure by polyacrylamide gel electrophoresis under denaturing conditions. Its steroid-binding characteristics are indistinguishable from SHBG in human serum (Avvakumov G V et al., 2000. J Biol Chem 275: 25920-25925). The in vitro assay involved the use of the purified human SHBG and [$^3$H]DHT as the labeled ligand. Human SHBG was treated for 30 min at room temperature with a dextran-coated charcoal (DCC) suspension in phosphate buffered saline (PBS) to remove any steroid ligand. After centrifugation (2,000×g for 10 min) to sediment the DCC, the supernatant containing the human SHBG was diluted in PBS to a concentration of 1 nM based on its steroid binding capacity.

Duplicate aliquots (100 μl) of this human SHBG solution were then incubated with an equal volume of [$^3$H]DHT at 10 nM, together with 100 μl of PBS alone or the same amount of PBS containing increasing concentrations of unlabeled steroid ligands as competitors in polystyrene test tubes. After incubation for 1 h at room temperature the reaction mixtures were placed in an ice bath for a further 15 min. Aliquots (600 μl) of an ice cold suspension of DCC were then added to each tube, and after a brief 2 seconds mixing, each tube was incubated in an ice bath for 10 min. The unbound ligands adsorbed to DCC were then removed by centrifugation (2,000×g for 15 min at 4° C.), and the amounts of [$^3$H]labeled DHT bound to SHBG were counted in 2 ml ACS scintillation cocktail using in liquid scintillation spectrophotometer. The average amounts of [$^3$H] labeled DHT bound to SHBG at each concentration of competitor (B) were expressed as a percentage of the average amounts of [$^3$H]labeled DHT bound to SHBG in the absence of competitor (T), and were plotted against the concentration of competitor in each assay tube.

The results of the competitive binding assays are depicted in FIG. 1. The data show that 15α-OH-T and 15β-OH-T do not bind human SHBG, when compared to DHT, T or DHEA in a competitive binding assay in which [$^3$H]DHT was used as labeled ligand. Therefore, in contrast to other androgens, the binding of 15α-OH-T or 15β-OH-T to human SHBG can be considered negligible.

The invention claimed is:

1. A pharmaceutical oral dosage unit containing at least 10 μg of an estrogen and at least 10 μg of a steroid selected from the group consisting of 15-hydroxytestosterones, precursors thereof, mixtures thereof and precursors of said mixtures; and a pharmaceutically acceptable excipient, wherein said oral dosage unit is selected from the group consisting of a tablet, a capsule and a chachet, wherein the precursors of the hydroxytestosterones are derivatives of the hydroxytestosterones wherein a hydrogen atom of at least one hydroxyl group has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue, and wherein the pharmaceutical oral dosage unit is orally active.

2. The pharmaceutical oral dosage unit according to claim 1, wherein the steroid is selected from the group consisting of 15α-hydroxytestosterone, precursors thereof, mixtures of 15α-hydroxytestosterone, and precursors of these mixtures of these hydroxytestosterones.

3. The pharmaceutical oral dosage unit according to claim 1, wherein the steroid is selected from the group consisting of 15β-hydroxytestosterone, precursors thereof, mixtures of 15β-hydroxytestosterone, and precursors of these mixtures of these hydroxytestosterones.

4. The pharmaceutical oral dosage unit according to claim 1, wherein the oral dosage unit is a tablet.

5. The pharmaceutical oral dosage unit according to claim 1, wherein the oral dosage unit contains between 20 μg and 1000 mg of the androgenic steroid.

6. The pharmaceutical oral dosage unit according to claim 1, wherein the oral dosage unit additionally contains at least 10 μg of a progestogen.

7. A method of hormone replacement therapy in a female mammal, said method comprising oral administration to said mammal of the oral dosage unit according to claim 1.

8. The method according to claim 7, wherein the method comprises the administration of the steroid in an average daily amount in the range of 0.5 µg to 1.5 mg per kg of bodyweight.

9. A method of contraception in a female mammal, said method comprising oral administration to said mammal of the oral dosage unit according to claim 1.

10. The method according to claim 9, wherein the method comprises the administration of the steroid in an average daily amount in the range of 0.5 µg to 1.5 mg per kg of bodyweight.

* * * * *